(12) United States Patent
Bock (10) Patent No.: US 10,252,044 B2
(45) Date of Patent: Apr. 9, 2019

(54) ULTRASONIC METHOD AND DEVICE FOR COSMETIC APPLICATIONS

(71) Applicant: Robert T. Bock, Brewster, NY (US)

(72) Inventor: Robert T. Bock, Brewster, NY (US)

(73) Assignee: ROBERT T. BOCK CONSULTANCY, LLC, Brewster, NY (US)

( * ) Notice: Subject to any disclaimer, the term of this patent is extended or adjusted under 35 U.S.C. 154(b) by 301 days.

(21) Appl. No.: 15/133,648

(22) Filed: Apr. 20, 2016

(65) Prior Publication Data

US 2016/0250457 A1    Sep. 1, 2016

Related U.S. Application Data

(63) Continuation-in-part of application No. 14/634,556, filed on Feb. 27, 2015.

(51) Int. Cl.
| | |
|---|---|
| *A61K 41/00* | (2006.01) |
| *A46B 5/00* | (2006.01) |
| *A46B 9/02* | (2006.01) |
| *A61M 37/00* | (2006.01) |
| *A46B 13/02* | (2006.01) |
| *A61B 17/00* | (2006.01) |

(52) U.S. Cl.
CPC ....... *A61M 37/0092* (2013.01); *A46B 5/0095* (2013.01); *A46B 9/021* (2013.01); *A46B 13/023* (2013.01); *A61K 41/0047* (2013.01); *A46B 2200/1046* (2013.01); *A61B 2017/00765* (2013.01); *A61M 2037/0007* (2013.01)

(58) Field of Classification Search
CPC .. A61M 37/0092; A46B 9/021; A46B 13/023; A61K 41/0047
USPC ........................................................... 604/22
See application file for complete search history.

(56) References Cited

U.S. PATENT DOCUMENTS

| | | | | |
|---|---|---|---|---|
| 5,618,275 | A * | 4/1997 | Bock | A61B 17/20 601/2 |
| 5,884,631 | A * | 3/1999 | Silberg | A61N 7/00 128/898 |
| 6,169,920 | B1 | 1/2001 | Haak | |
| 6,322,532 | B1 | 11/2001 | D'Sa | |
| 7,269,873 | B2 * | 9/2007 | Brewer | A46B 15/0002 15/22.1 |
| 8,016,810 | B2 | 9/2011 | Levin | |
| 8,386,027 | B2 | 2/2013 | Chuang | |
| 8,700,176 | B2 | 4/2014 | Azar | |
| 2001/0025190 | A1 * | 9/2001 | Weber | A61B 18/1402 607/89 |
| 2003/0181897 | A1 * | 9/2003 | Thomas | A61B 17/0625 606/21 |

(Continued)

*Primary Examiner* — Edelmira Bosques (57) ABSTRACT

A combination of low frequency high amplitude sonic frequency vibrations and high frequency low intensity ultrasonic pressure waves are applied to cosmetic compounds and to the skin to promote improved penetration of the cosmetic compounds into the epidermis. The cosmetic applicator device includes means for generating both sonic frequency vibrations and ultrasonic pressure waves adopted to deliver cosmetic compounds into the epidermis safely without significant temperature rise in the skin. Various removable applicator and skin cleaning attachments are also disclosed, including some with ultrasound waveguide.

1 Claim, 8 Drawing Sheets

(56) References Cited

U.S. PATENT DOCUMENTS

| | | | | |
|---|---|---|---|---|
| 2005/0091770 A1* | 5/2005 | Mourad | ............ | A46B 15/0002 |
| | | | | 15/22.1 |
| 2007/0011836 A1* | 1/2007 | Brewer | ............ | A46B 15/0002 |
| | | | | 15/220.1 |
| 2009/0211042 A1* | 8/2009 | Bock | ............ | A46B 13/023 |
| | | | | 15/22.1 |
| 2009/0318853 A1* | 12/2009 | Reed | ............ | A61M 35/003 |
| | | | | 604/22 |

\* cited by examiner

ULTRASONIC METHOD AND DEVICE FOR COSMETIC APPLICATIONS

CROSS REFERENCE TO RELATED APPLICATIONS

This is a Continuation-in-Part application of Ser. No. 14/634,556 filed Feb. 27, 2015, the contents of which are hereby incorporated by reference in their entireties as if fully set forth herein.

FIELD OF THE INVENTION

This invention relates to sonic and/or ultrasonic devices for cosmetic applications.

BACKGROUND OF THE INVENTION

The stratum corneum, the outermost layer of the epidermis consists of dead cells (corneocytes). The purpose of this layer of dead skin is to form a barrier to protect underlying living tissue from infection, dehydration, and chemical attacks.

Unfortunately, the same low permeability barrier characteristic of the stratum corneum, which protects the body from infections, also resists the penetration of beneficial cosmetic and chemical compounds, such as moisturizers, alpha-hydroxyl acids, collagen, vitamins and vasodilators. In addition, oily and congested skin conditions are also reducing the penetration of beneficial skin treatment compounds.

The invention is concerned with methods and apparatus facilitating the use of sonic and ultrasonic energy coupled to the skin to temporarily increase the permeability of the skin and enhance the absorption of beneficial cosmetic and chemical compounds into the skin, and particularly to direct and focus the ultrasound energy into small restricted areas such as the nose and face interface by the utilization of an ultrasound waveguide.

DESCRIPTION OF PRIOR ART

Numerous attempts have been made in the past to enhance the penetrations of cosmetic compounds into the skin by chemical, electrical and ultrasonic means.

The application of chemicals to modify the skin structure to allow the penetration of cosmetics was found to be dangerous because while it provided access for cosmetics to penetrate, it left the body unprotected against harmful environments, interacting with corneocytes causing irritation, erythema (red skin) and contact dermatitis.

The application of electrical fields to create transient transport pathways by a method called electroporation, and the method to electrically charge molecules to increase their penetration into the skin called iontophoresis (U.S. Pat. No. 6,169,920), have both been proven costly and ineffective. Electrical abrasion devices for increasing the skin's permeability (U.S. Pat. No. 8,386,027) remove some layers of the stratum corneum causing intense irritation and discomfort.

The effort of prior art of ultrasonically induced drug delivery (sonophoresis) described in U.S. Pat. No. 6,322,532 is focused in driving drug molecules through the skin by high frequency and high intensity ultrasonic pressure waves. This procedure suffers from the disadvantage of tissue heating and the associated modification and sometimes destruction of healthy cells.

To achieve a non tissue heating modality, ultrasound devices described by McDaniel (US 2001/0041856), Reed (US 2009/0318853 A1), and Bock (U.S. Pat. No. 5,618,275) are typically operate at 35 mW/cm$^2$ intensity and utilizing ultrasound transducers of 12 mm diameter and larger. While these devices are highly suitable for use on large flat surface areas of the face, these devices will not fit into and cannot apply the compounds into restricted areas such as the intersection of the face and the nose and particularly between the eyes and the nose. Merely creating a smaller device to fit into these restricted areas would defeat the purpose of having a general purpose application device for the larger flat areas of the face.

Notwithstanding the teaching of the prior art, the ability to deliver cosmetic compounds into the skin by a general purpose device for both in small and restricted areas and the large flat areas of the face safely and effectively has remained unsolved.

Responding to the above described unresolved needs, the object of this invention is to provide a general purpose skin care apparatus to safely increase the permeability of the stratum corneum and deliver cosmetic compounds deeply into the dermis in both the small and restricted areas and the large flat areas of the face.

SUMMARY OF THE INVENTION

As noted in the description of the prior art, the safety of the typical sonophoresis apparatus is compromised by the high intensity requirements of the process, resulting in excessive tissue heating and its associated consequences.

An objective of the invention is to improve the safety of typical sonophoresis apparatus to deliver cosmetic compounds into the dermis at reduced ultrasound intensity, particularly in small and restricted areas of the face, such as between the eyes and the nose.

The invention achieves this objective of utilizing lower intensity ultrasonic pressure waves by augmenting the ultrasonic pressure waves with non-tissue heating low frequency sonic vibrations applied to the skin in combination with the high frequency ultrasound. The low frequency sonic vibration component of this new method increases the permeability of the skin and allows a lower intensity non-tissue heating ultrasound component to drive the cosmetic compound through the stratum corneum into the dermis. Furthermore, since oils and various contaminants on the skin can reduce the penetration of cosmetic compounds, an optional pre treatment skin-cleansing step is part of the disclosed method. To reach into small and restricted areas, the invention utilizes slim metallic ultrasound waveguides.

In the above discussion, the terms cosmetic compounds and vasodilators includes but not limited to skin care products such as anti wrinkle lotions, moisturizers, antioxidant vitamins, alpha-hydroxyl acids, liposomes, collagen, elastin, hair growth and hair remover compounds and others.

DESCRIPTION OF THE PREFERRED EMBODIMENTS

Figure 1:
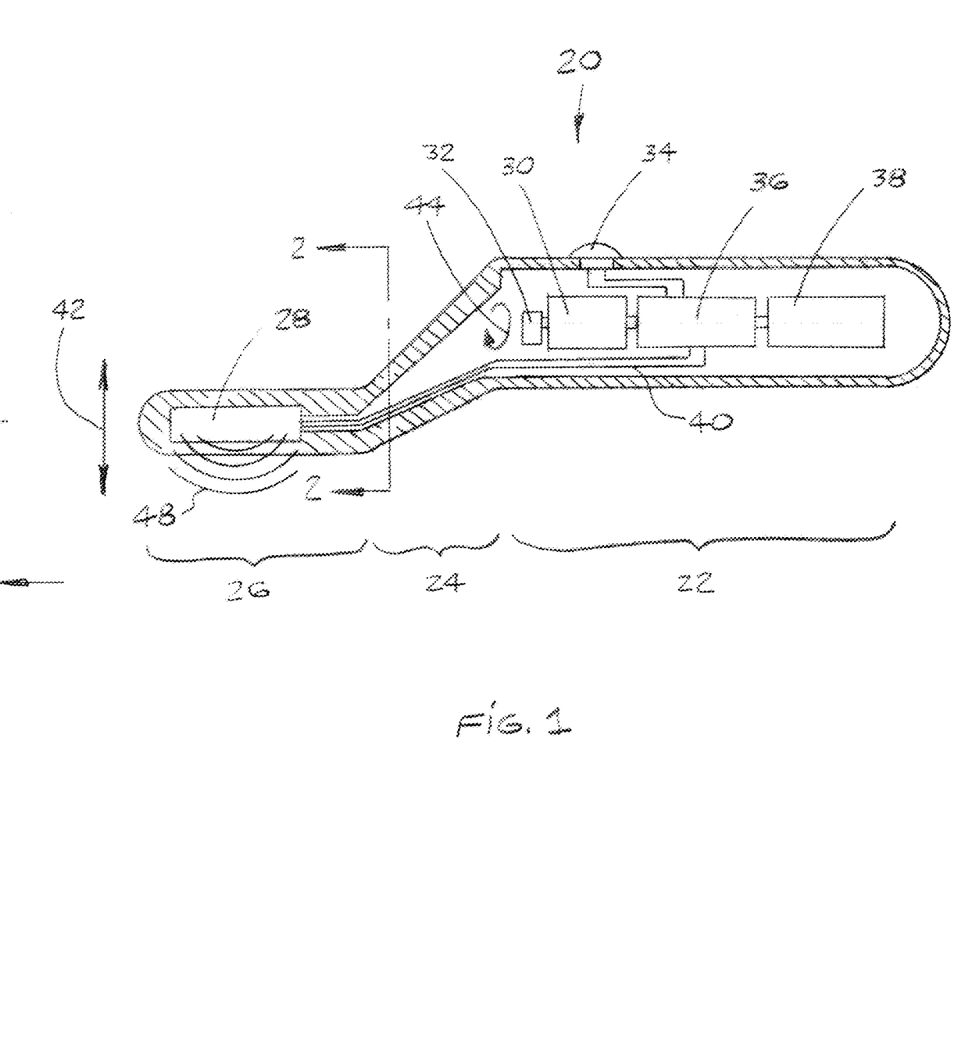
FIG. 1 shows a longitudinal cross section of the invention consisting of the device handle, the motion transducer neck, the applicator portion including an ultrasonic transducer, the driving motor, electronic controls and battery.
Figure 2:
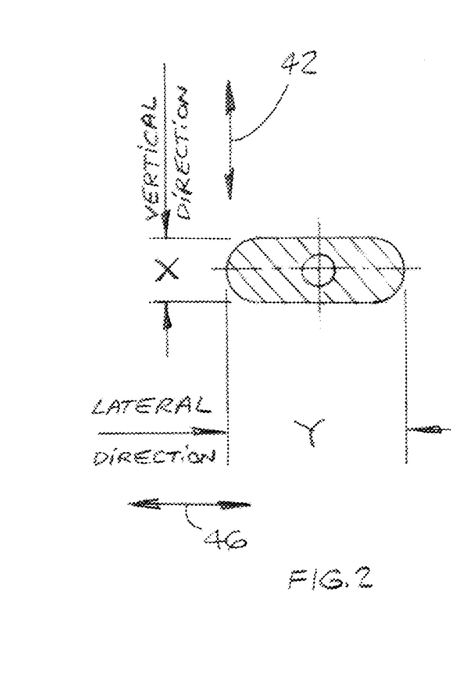
FIG. 2 shows the cross section of the neck of the device, which is configured to act as a motion transducer.

FIG. 1 and FIG. 2 show the invention of the ultrasonic cosmetic applicator 20 in a preferred configuration. The applicator 20 comprises a tubular shaped handle portion 22, a neck portion 24, and an applicator head portion 26 constructed of a rigid plastic material such as Acrylonitrile Butadiene Styrene (ABS), an ultrasound transducer 28, a driving motor 30, an eccentric weight 32 mounted on the output shaft of the driving motor 30, an electronic module 36, a battery pack 38, and interconnecting wiring 40.

The ultrasound transducer 28 is typically constructed of a piezo-electric ceramic material such as PZT-8 grade Lead Zirconate Titanate manufactured by Morgan Matroc, Inc., or similar products manufactured by numerous other entities. The construction of the ultrasound transducer 28 can be a single or a multiple element unit, as it is commonly practiced by people familiar in the art.

The ABS material utilized for the applicator 20 is due to the ABS excellent acoustic characteristics. However, numerous other rigid plastic materials could be substituted to achieve various cost and performance goals of the designers.

Control switch 34 energizes the driving motor 30, which rotates the eccentrically mounted weight 32 between 2,000 and 25,000 RPM, ideal speed being at 9,000 RPM, generating a 33 to 417 Hertz sonic frequency rotational vibration 44 of the handle 22 and neck 24 portions of the applicator 20, which is considered a relatively low sonic frequency vibration in the art, which defines sonic frequency vibration as being 10 to 20,000 Hertz. As shown in FIG. 2 the cross section of the neck 24 is designed to be relatively thin in the vertical direction X compared to the lateral direction Y thereby significantly increasing the vertical vibration 42 amplitude of the applicator head 26 while significantly decreasing lateral vibration 46 amplitude of the applicator head 26. In other words, the neck portion 24 of the applicator 20 is designed to be a motion transducer to convert the rotational vibration 44 of the handle 22 portion of the applicator 20 into a substantially vertical vibration 42 of the applicator head 26, converting the rotational energy of the motor 30 into vertically vibrating energy of the applicator head 26.

The battery pack 38 can be constructed as a single cell or multi cell battery pack, of various chemistries, such as Alkaline Manganese, Nickel-Cadmium, Ni-Mh, Lithium or other newer construction.

The major function of the electronic module 36 is to convert the low voltage DC power, typically 1.5 to 4.8 VDC, of the battery pack 38 into high voltage (4.8 to 60 Volt) typically sinusoidal wave ultrasonic frequency (typically 15 kHz to 20 MHz) DC power in a continuous wave or burst wave modality.

Simultaneously with energizing the driving motor 30, switch 34 also activates the electronic module 36. Through the interconnecting wiring 40 the electronic module 36 energizes the ultrasound transducer 28 which contracts and expands in tune with the high frequency DC power and converts this electronic power into ultrasonic pressure waves 48 at a typical intensity from 0.05 to 0.5 W/cm$^2$.

Figure 3A:
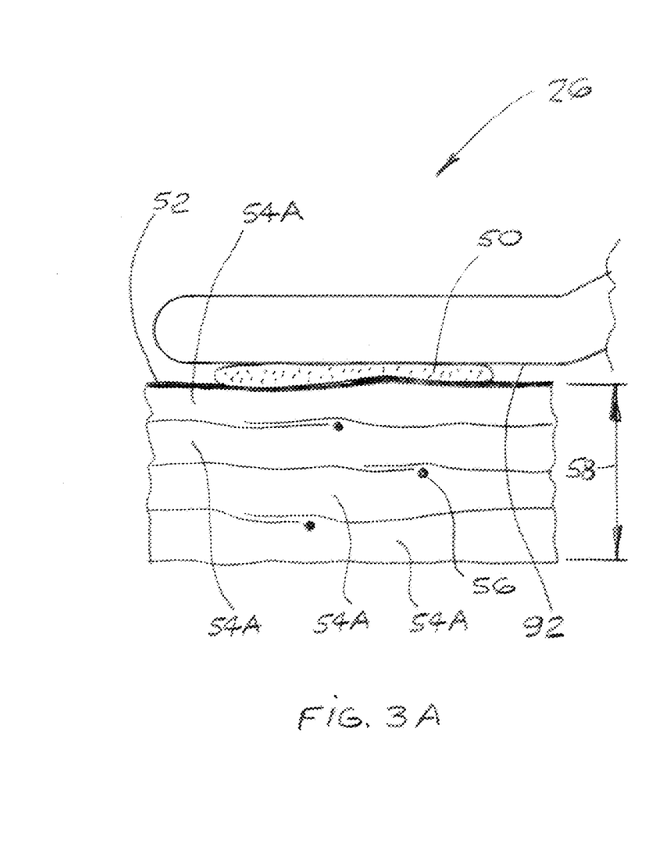
FIG. 3A shows the applicator head of the device in contact with the skin.

In FIG. 3A the applicator head 26 of the applicator 20 is shown in position on top of the outer surface of the stratum corneum 52, consisting of flat dead cells filled with keratin fibers surrounded by ordered lipid bilayers 54A shown in a relaxed position 58. The ordered structure of the stratum corneum 52 and the ordered lipid bilayers 54A are forming a normally almost impermeable skin structure. A thin layer of cosmetic compound 50 is shown to be disposed between the applicator contact surface 92 of the applicator head 26 and the stratum corneum 52. A typically very limited amount of small molecules 56 of the cosmetic compound 50 are shown to be penetrating slightly into the ordered lipid bilayers 54A without assistance from the applicator head 26.

Figure 3B:
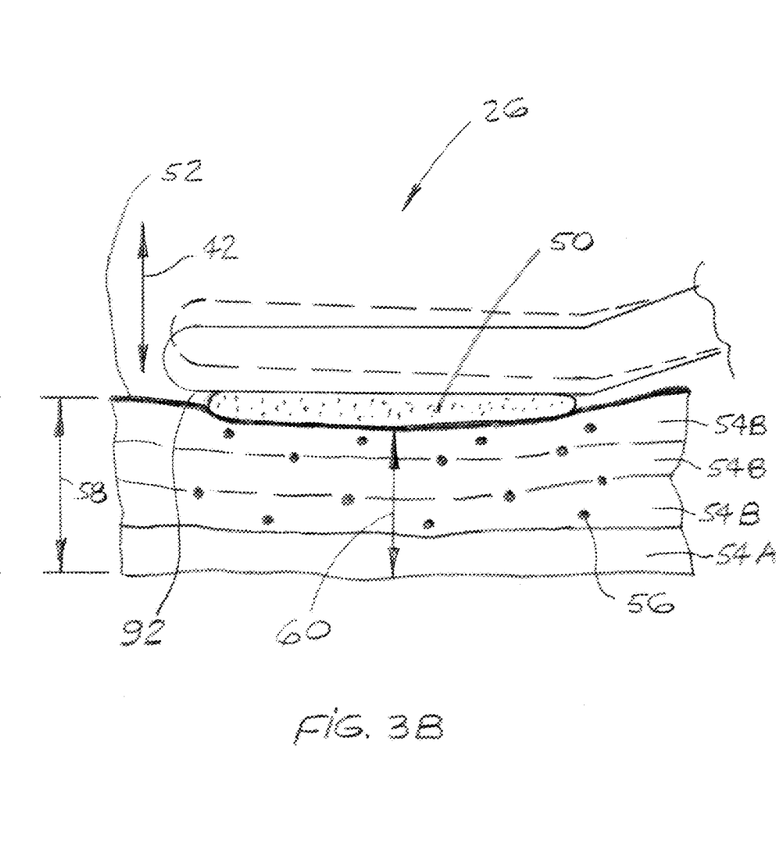
FIG. 3B illustrates the sonic frequency component of the device and its effects on the stratum corneum.

FIG. 3B shows the applicator head 26 activated in the vertically vibrating 42 mode on top of the stratum corneum 52 and a thin layer of cosmetic compound 50 is shown to be disposed between the applicator contact surface 92 of the applicator head 26 and the stratum corneum 52. The vertical vibration 42 of the applicator head 26 (also depicted with solid and dashed lines to illustrate vibration) repeatedly compresses and relaxes the stratum corneum 52 and the ordered lipid bilayers 54A from the relaxed position 58 to the compressed position 60 in tune with the high amplitude low frequency vibration mode of the applicator head 26. Under the repeated and continuing influence of this high amplitude low sonic frequency vibration 42 and the resulting repeated compression and relaxation cycles of the stratum corneum 52 and the ordered lipid bilayers 54A, the ordered lipid bilayers 54A beginning to disorganize and develop larger passage ways for the molecules 56 of the cosmetic compound 50 to pass through. The disorganized lipid bilayers 54B are depicted with dashed lines.

Figure 4:
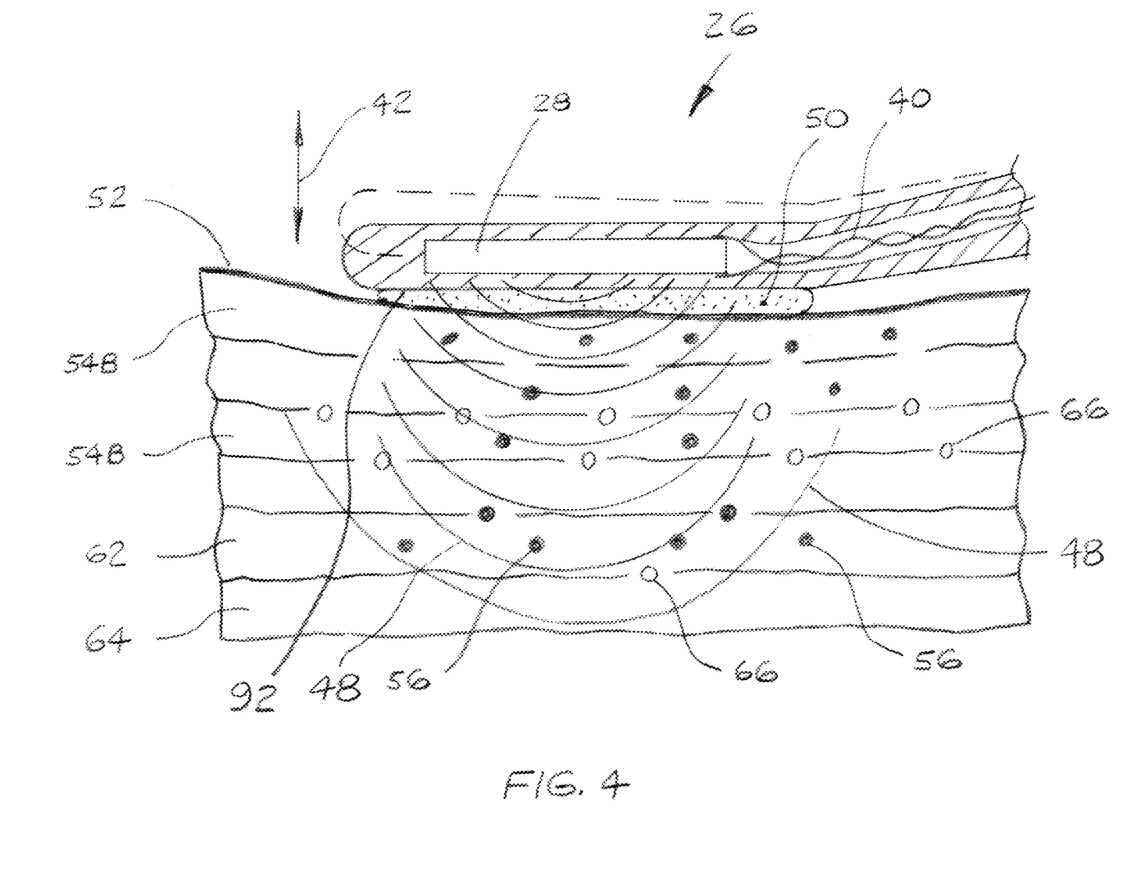
FIG. 4 illustrates the simultaneous application of the sonic frequency vibration and ultrasound pressure wave components of the device and their combined effects on the stratum corneum.

FIG. 4 shows the applicator head 26 in contact with the stratum corneum 52 while having a thin layer of cosmetic compound 50 disposed between the applicator contact surface 92 of the applicator head 26 and the stratum corneum 52. The ultrasound transducer 28 is shown being energized by the electronic module 36 through the connective wiring 40 and radiating ultrasonic pressure waves 48 into the stratum corneum 52 and the disorganized lipid bilayers 54B. While the sonophoresis art has been demonstrated to work in the frequency range of 20 kHz to 20 MHz and in both of a continuous wave and a burst wave modality, it is important to select the right combination of frequency, driving voltage, and modality to match the size and characteristics of the piezo electric transducer selected for the system. Hard piezo materials such as the PZT8 formulation will output high ultrasonic power intensities with the associated heating of tissues when driven by high voltages. To avoid overheating the tissue, a 20% duty cycle (20% on 80% off) burst modality has been proven helpful in prior art.

Now, according to the invention, safety of the sonophoresis process can be further enhanced by the simultaneous application of a non tissue heating high amplitude low sonic frequency mechanical vibration 42 and the ultrasonic pressure waves 48 to the stratum corneum 52. Due to the presence of the high amplitude low sonic frequency vibration 42 applied to the stratum corneum 52, which establishes the initial pathways through the stratum corneum 52, the intensity of the ultrasonic pressure waves 48 can be reduced significantly, resulting in proportional reduction of tissue heating, while maintaining the effectiveness of the process.

The high frequency ultrasonic pressure waves 48, as shown in FIG. 4, penetrate the disorganized lipid bilayers 54B much deeper than the lower sonic frequency vibrations 42 do. These ultrasonic pressure waves 48 in a preferred frequency range of 20 kHz to 2 MHz and in a 20% duty cycle burst modality are developing mild cavitation deep within the lipid bilayers 54B resulting in microscopic air and/or vacuum pockets 66 which act to further break up the organized lipid bilayers 54A shown in FIG. 3A into disorganized lipid bilayers 54B, generating more and deeper passage ways for the cosmetic compound molecules 56 to penetrate through the stratum corneum 52, through the disorganized lipid bilayers 54B, through the bottom layer of the epidermis 62 and into the dermis 64.

Figure 5:
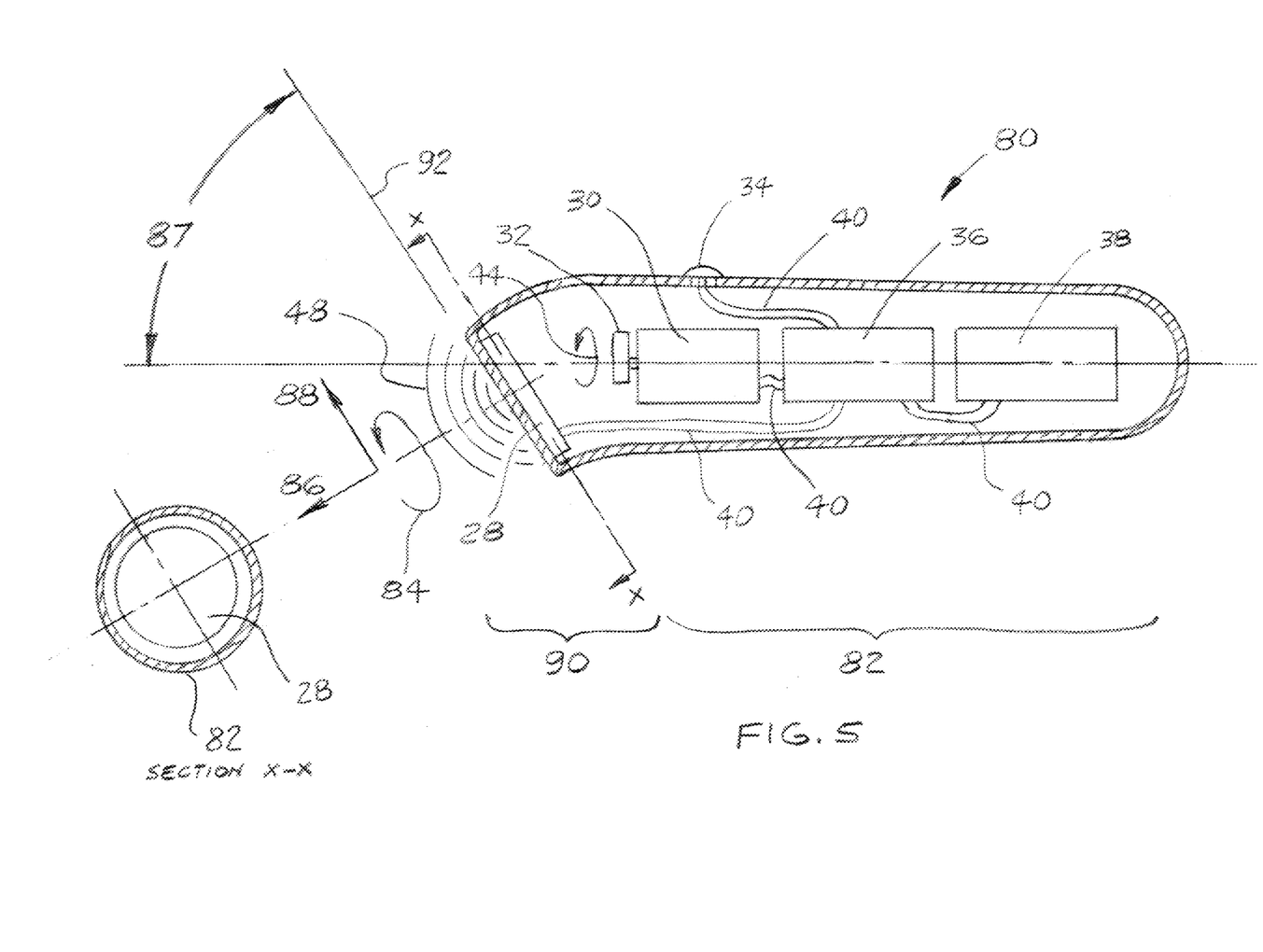
FIG. 5 shows a longitudinal cross section of an alternative configuration of the invention.

FIG. 5 shows a longitudinal cross section of an alternative configuration of the invention wherein the applicator 80 comprises a tubular shaped handle portion 82 terminating in an angular applicator head portion 90 constructed of a rigid plastic material such as Acrylonitrile Butadiene Styrene (ABS), an ultrasound transducer 28, a driving motor 30, an eccentric weight 32 mounted on the output shaft of the driving motor 30, an electronic module 36, a battery pack 38, and interconnecting wiring 40.

The ultrasound transducer 28 is typically constructed of a piezo-electric ceramic material such as PZT-8 grade Lead Zirconate Titanate manufactured by Morgan Matroc, Inc., or similar products manufactured by numerous other entities. The construction of the ultrasound transducer 28 can be a single or a multiple element unit, as it is commonly practiced by people familiar in the art.

The ABS material utilized for the applicator 80 is due to the ABS excellent acoustic characteristics. However, numerous other materials could be substituted to achieve various cost and performance goals of the designers. For example, the applicator contact surface 92 may be constructed of stainless steel or other metallic material.

Control switch 34 energizes the driving motor 30, which rotates the eccentrically mounted weight 32 between 2,000 and 25,000 RPM, ideal speed being at 9,000 RPM, generating a 33 to 417 Hertz sonic frequency rotational vibration 44 of the handle portion 82 of the applicator 80.

The angular positioning 87 of the applicator contact surface 92 of the applicator head portion 90 acts as a motion transducer converting the rotational vibration 44 of the handle portion 82 into an angular rotational vibration 84 of the applicator contact surface 92 of the applicator head portion 90. The angular rotational vibration 84 creates a two dimensional vibration motion of the applicator contact surface 92 in the directions of motion vector 86 and motion vector 88.

While FIG. 5 depicts an angularly fixed applicator head portion 90 construction, applicator 80 can also be constructed having a user adjustable angular applicator head portion 90 wherein the user can vary the angular positioning 87 of the applicator contact surface 92 to increase or decrease the vibratory motion in the directions of motion vector 86 and motion vector 88. A decreasing angle 87 will decrease the vibration amplitude of motion vector 88 and increase the vibration amplitude of motion vector 86.

The battery pack 38 can be constructed as a single cell or multi cell battery pack, of various chemistries, such as Alkaline Manganese, Nickel-Cadmium, Ni-Mh, Lithium or other newer construction.

The major function of the electronic module 36 is to convert the low voltage DC power, typically 1.5 to 4.8 VDC, of the battery pack 38 into high voltage (4.8 to 60 Volt) typically sinusoidal wave ultrasonic frequency (typically 15 kHz to 20 MHz) DC power in a continuous wave or burst wave modality.

Simultaneously with energizing the driving motor 30, switch 34 also activates the electronic module 36. Through the interconnecting wiring 40 the electronic module 36 energizes the ultrasound transducer 28 which contracts and expands in tune with the high frequency DC power and converts this electronic power into ultrasonic pressure waves 48 at a typical intensity from 0.05 to 0.5 W/cm$^2$.

The embodiment of the invention as applicator 80 depicted in FIG. 5 functions the same way as the embodiment of the invention as applicator 20 depicted in FIGS. 1, 2, 3A, 3B, and 4. More particularly, the sonic frequency vibration of the applicator contact surface 92 of the applicator head portion 90 in the direction of motion vector 86 described in FIG. 5 functions the same way as the sonic frequency vibration of the applicator contact surface 92 of applicator head portion 26 in the direction of motion vector 42 described in FIG. 3B and FIG. 4. The ultrasonic pressure waves 48 radiated from applicator 80 described in FIG. 5 function the same way as the ultrasonic pressure waves 48 radiated from applicator head 26 described in FIG. 4. The underlying science of the two embodiments are identical.

Figure 6:
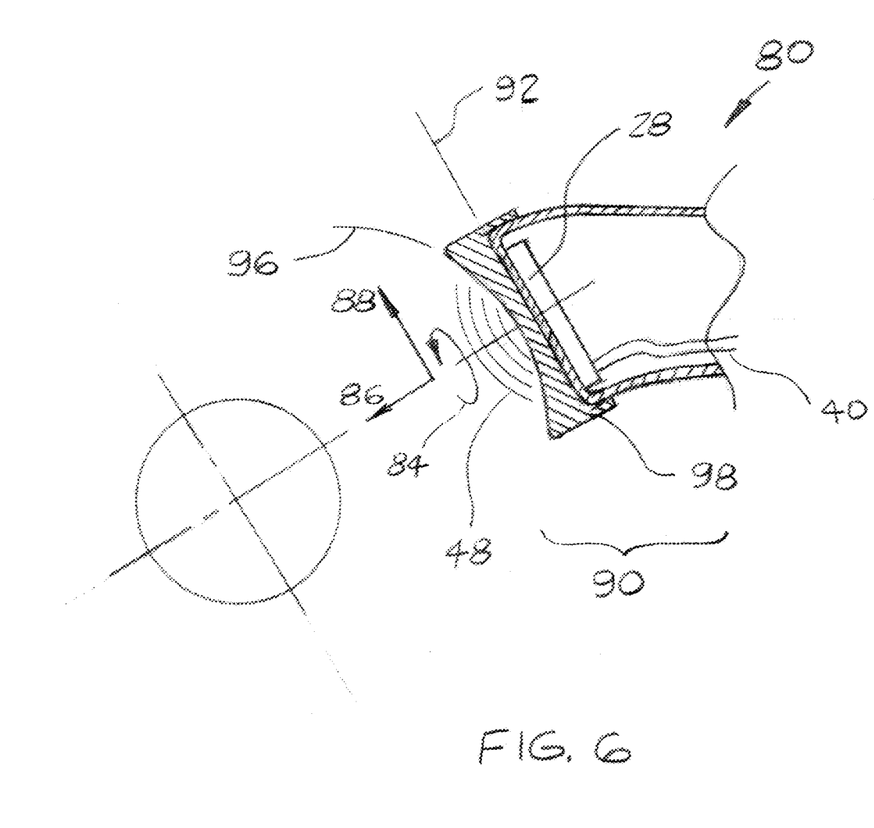
FIG. 6 shows a removable applicator head designed for convex areas of the anatomy.

FIG. 6 shows a applicator head 98 designed to conduct the low frequency orbital vibration 84 and vibration motion vectors 86 and 88 and the ultrasound pressure waves 48 into the hard convex areas of the anatomy, such as the scalp, the elbows, and similar areas.

The applicator contact surface 92 of the applicator head portion 90 as described earlier in FIG. 5 is typically made of rigid or semi rigid material designed for soft flexible surfaces of the anatomy, such as the cheeks, where the anatomy conforms to the applicator contact surface 92 under slight pressure and transmission of the ultrasonic pressure waves 48 to the anatomy is easily achieved. However, when the flat rigid applicator contact surface 92 is applied to a hard convex area, such as the scalp, it results in a very small single point contact, which limits the transmission of the ultrasonic pressure waves to the anatomy.

To maximize transmission of the ultrasonic pressure waves 48 to the hard convex areas of the anatomy the applicator head 98 is made of a flexible ultrasound conductive material such as silicone rubber and features a concave contact surface 96 which easily conforms to the anatomy under slight pressure. The thickness of the soft silicone rubber material at the central point must be minimized in the sub-millimeter region to minimize ultrasound attenuation losses by the soft silicone rubber material. To further assure excellent transmission of the ultrasound pressure waves 48 from the ultrasound transducer 28 to the applicator head 98 a slight coating of ultrasound conductive material such as water or contact gel can be applied between the applicator contact surface 92 and the removable applicator head 98.

The applicator head 98 design depicted in FIG. 6 can be executed either as permanently fixed to the applicator 80 or constructed to be easily removable for replacement or exchange with other optional accessories of the device.

Figure 7A:
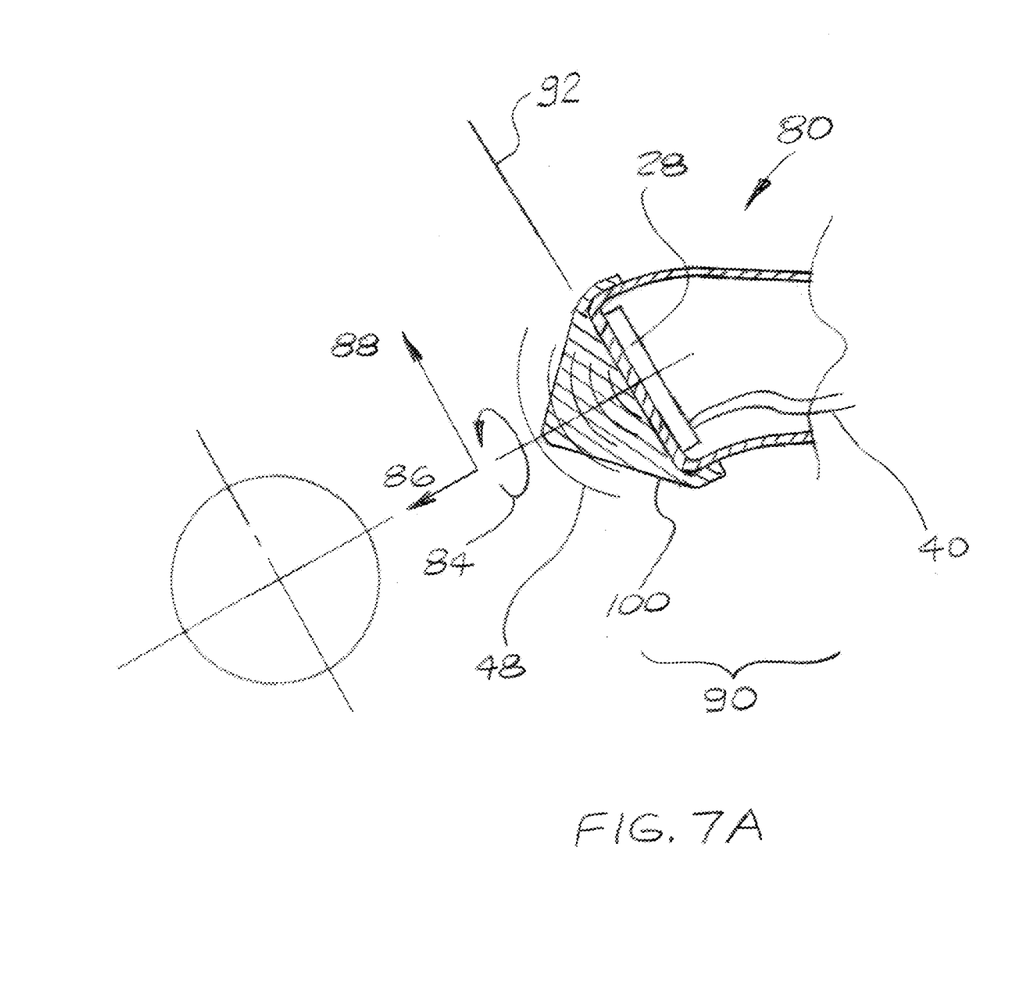
FIG. 7A shows a removable applicator head designed for concave areas of the anatomy.

FIG. 7A shows a simple inexpensive cone shaped applicator head 100 designed for concave areas of the anatomy.

Such small concave areas as between the eyes and the nose or between the cheeks and the nose are typically not accessible by the flat applicator contact surface 92 of the applicator head portion 90 of applicator 80 designed for larger soft surfaces of the anatomy. The applicator head 100 is constructed of flexible materials, such as flexible silicone rubber conducting the low frequency orbital vibration 84 and vibration motion vectors 86 and 88 and the ultrasound pressure waves 48 into these small concave areas. While the conical shape of the applicator head 100 allows the contact with the restricted areas, the ultrasound pressure waves 48 must travel through a long path of 20 mm or longer ultrasound attenuating flexible plastic material, which significantly attenuates the ultrasound pressure waves 48 emitted by transducer 28, reducing the effectiveness of the device.

The applicator head 100 design depicted in FIG. 7A can be executed either as permanently fixed to the applicator 80 or constructed to be easily removable for replacement or exchange with other optional accessories of the device.

Figure 7B:
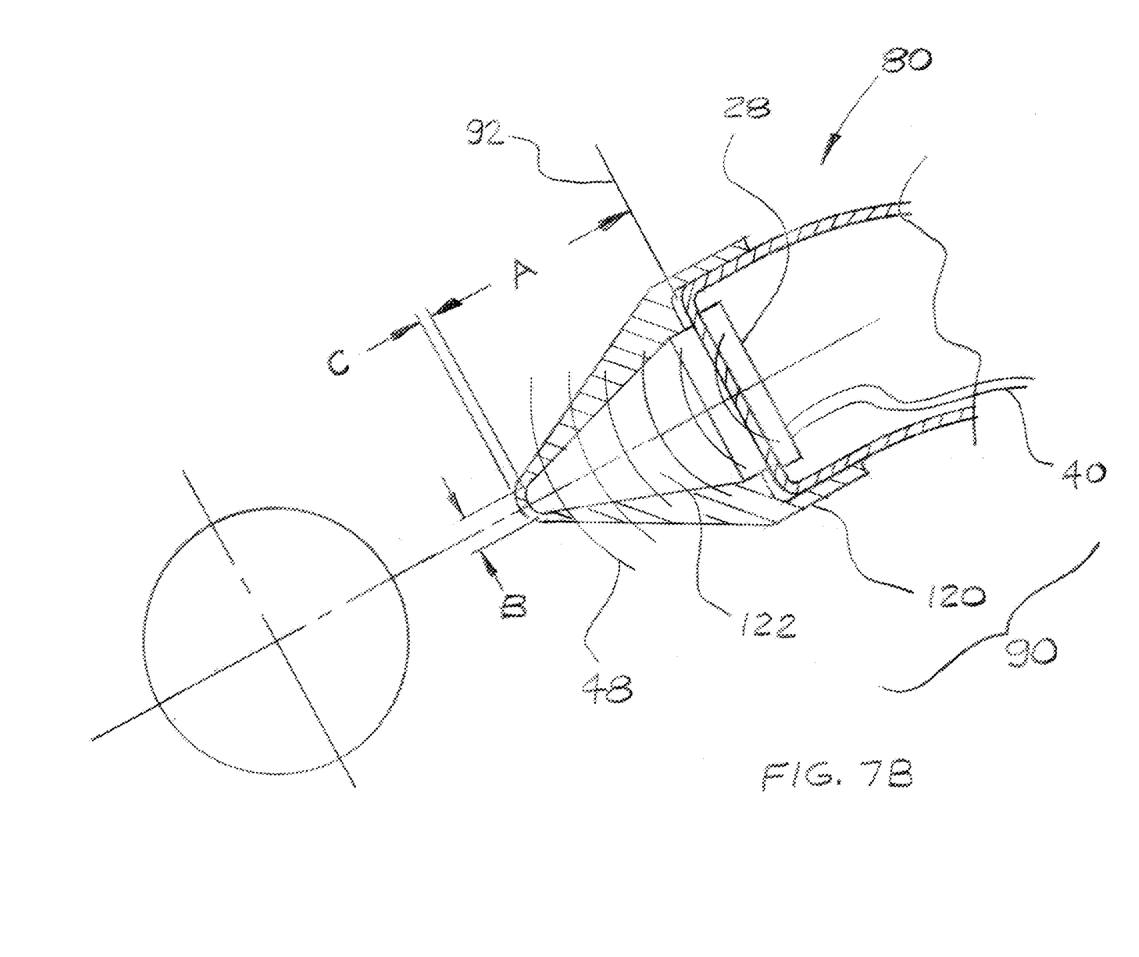
FIG. 7B shows a removable applicator head designed for concave areas of the anatomy having an ultrasound waveguide.

FIG. 7B depicts a solution to the excessive ultrasound pressure waves 48 attenuation described in FIG. 7A, which eliminates the attenuation of the ultrasound pressure waves 48 emitted by the ultrasound transducer 28 and allow the ultrasound pressure waves 48 to reach the small and restricted areas between the eyes and the nose practically un-attenuated. The invention employs a conically shaped non-attenuating ultrasound waveguide 122 insert within the applicator head 120 made of metal such as aluminum, titanium or similar metals in solid contact with the flat applicator surface 92 of the applicator head portion 90 of the device. Aluminum or titanium metal is preferred for the waveguide due to their light weight and their non-attenuating characteristic of the ultrasound pressure waves 48. The waveguide 122 is a long aspect ratio design, typically having a ratio of 4 to 1 or larger between the length A and the tip diameter B. The larger base diameter of the waveguide 122 is designed to match the size of the ultrasound transducer 28 in the applicator head portion 90 of the device. Tip diameter B is typically ranges between 4 mm and 6 mm. The tapered construction of waveguide 122 focuses the acoustic energy from the larger ultrasound transducer 28 into the smaller tip diameter B and increases the efficiency of the device.

The shell of the applicator head 120 surrounding and securing the metallic ultrasound waveguide 122 is typically made of a flexible material, such as silicone rubber to provide a pleasant tactile feeling for the user. Dimension C shown at the tip of the applicator head 120 should be minimized to 1 mm or less to reduce the attenuation of the ultrasound pressure waves 48 reaching the skin of the user.

The applicator head 120 design depicted in FIG. 7B can be executed either as permanently fixed to the applicator 80 or constructed to be easily removable for replacement or exchange with other optional accessories of the device.

Figure 8:
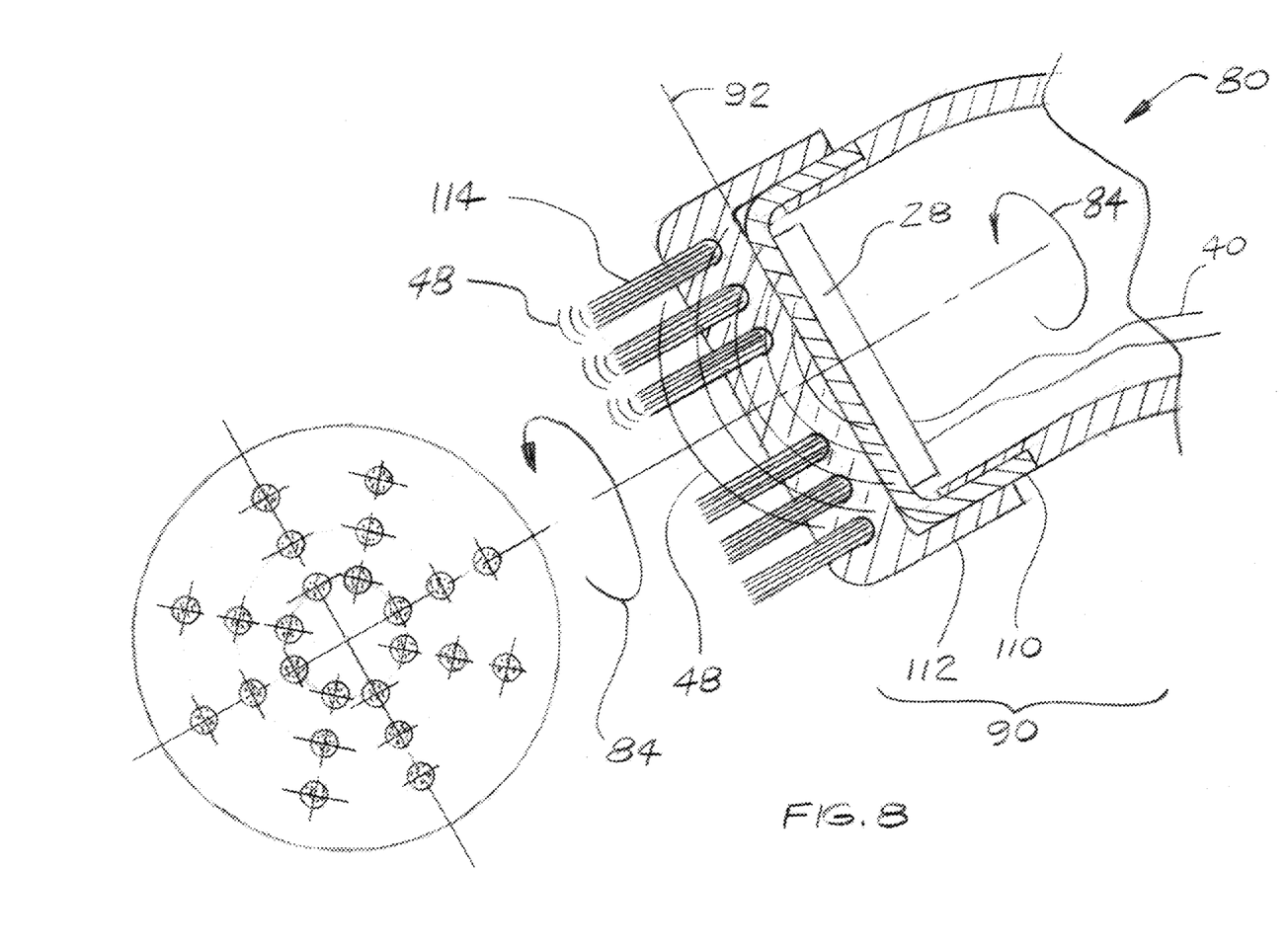
FIG. 8 shows a removable brush head for cleansing the skin.

FIG. 8 shows a removable cleansing brush head 112 installed on the applicator head portion 90 of applicator 80. The brush head 112 is typically constructed of a semi rigid ABS plastic material housing multiple tufts of bristles 114.

As described in detail in FIG. 5 the applicator motor 30 vibrates the applicator head portion 90 in an orbital vibration 84 pattern. This orbital vibration 84 is transferred to the brush head 112 and the plurality of bristle tufts 114. When energized through the interconnecting wiring 40 the ultrasound transducer 28 generates and emits ultrasound pressure waves 48 which are conducted by the applicator contact surface 92 to the brush head 112 and the bristle tufts 114 and radiated from the bristle tufts 114 to the skin of the user. Applying slight pressure of the orbitally vibrating 84 bristle tufts 114 against the skin the user effectively cleansing the skin by the synergistic scrubbing action of the bristle tufts 114 and the ultrasound pressure waves 48 radiated by the bristle tufts 114.

FIG. 8 also shows an optional construction of the applicator head portion 90 incorporating a stainless still cup 110.

While the preceding description contains much specificity, these should not be construed as limitations on the scope of the invention, but rather as an exemplification of preferred and additional embodiments thereof. Skilled artisans will readily be able to change dimensions, shapes, and construction materials of the various components described in the embodiments and adopt the invention to various types of sonic and ultrasonic energy applications. For example, additional removable and interchangeable applicators for enhanced cleansing of the skin such as sponges, cotton pads, lotion dispensers enhanced by the sonic and ultrasonic frequency motion of the applicator head are possible. Accordingly, the scope of the invention should be determined not by the embodiments illustrated, but by the appended claims and their legal equivalents.

What is claimed:
1. A cosmetic applicator comprising:
a) a handle portion and an applicator head portion;
b) said applicator head portion having an ultrasound transducer operative to produce non-attenuated ultrasonic pressure waves at frequencies between 20 kHz and 20 MHz; and
c) an ultrasound waveguide acoustically coupled to said ultrasound transducer operative to transmit said non-attenuated ultrasound pressure waves by direct contact with and into a skin to facilitate enhanced penetration of cosmetic compounds into said skin;
d) said handle portion having means to generate ultrasonic frequency electric signals and transmitting said electric signals to power said ultrasound transducer; and
e) a motor mounted in said handle portion to generate sonic frequency orbital vibrations in the range of about 33 to about 250 Hz of said applicator head operative to increase permeability of said skin; and
f) a conically shaped solid metal core ultrasound waveguide acoustically coupled to said ultrasound transducer, operational to focus and transmit said non-attenuated ultrasound pressure waves by direct contact with and into small restricted areas of the facial anatomy.

* * * * *